(12) United States Patent
Hlatky et al.

(10) Patent No.: US 6,864,210 B2
(45) Date of Patent: Mar. 8, 2005

US006864210B2

(54) BIMETALLIC OLEFIN POLYMERIZATION CATALYSTS CONTAINING INDIGOID LIGANDS

(75) Inventors: Gregory G. Hlatky, Morrow, OH (US); Jonathan L. Schuchardt, Royersford, PA (US)

(73) Assignee: Equistar Chemicals, LP, Houston, TX (US)

( * ) Notice: Subject to any disclaimer, the term of this patent is extended or adjusted under 35 U.S.C. 154(b) by 86 days.

(21) Appl. No.: 10/359,890

(22) Filed: Feb. 6, 2003

(65) Prior Publication Data

US 2004/0157730 A1 Aug. 12, 2004

(51) Int. Cl.$^7$ ............................................. B01J 31/00
(52) U.S. Cl. ................... 502/150; 502/152; 502/102; 502/103; 526/114; 526/131; 525/421
(58) Field of Search ................. 502/150, 152, 502/102, 103; 525/421; 526/114, 131

(56) References Cited

U.S. PATENT DOCUMENTS

| | | |
|---|---|---|
| 622,139 A | 3/1899 | Gifford |
| 662,073 A | 11/1900 | Koetschet |
| 718,340 A | 1/1903 | Graul |
| 765,576 A | 7/1904 | Graul |
| 836,309 A | 11/1906 | Engi |
| 841,003 A | 1/1907 | Engi |
| 848,354 A | 3/1907 | Engi |
| 856,687 A | 6/1907 | Engi |
| 867,306 A | 10/1907 | Schirmacher et al. |
| 867,715 A | 10/1907 | Engi |
| 872,115 A | 11/1907 | Engi |
| 872,227 A | 11/1907 | Engi |
| 888,852 A | 5/1908 | Schirmacher et al. |
| 892,897 A | 7/1908 | Schirmacher et al. |
| 899,863 A | 9/1908 | Engi et al. |
| 916,030 A | 3/1909 | Schmidt et al. |
| 949,592 A | 2/1910 | Münch |
| 963,813 A | 7/1910 | Schmidt et al. |
| 1,133,031 A | 3/1915 | Hutzler |
| 1,211,413 A | 1/1917 | Cone |
| 1,564,218 A | 12/1925 | Dow |
| 1,590,685 A | 6/1926 | Herz et al. |
| 1,954,707 A | 4/1934 | Lubs et al. ............ 260/108 |
| 4,966,977 A | 10/1990 | Takaki et al. ............ 548/457 |
| 5,153,157 A | 10/1992 | Hlatky et al. ............ 502/117 |
| 5,198,401 A | 3/1993 | Turner et al. ............ 502/155 |
| 5,241,025 A | 8/1993 | Hlatky et al. ............ 526/129 |
| 5,414,180 A | 5/1995 | Geerts et al. ............ 585/525 |
| 5,648,440 A | 7/1997 | Sugano et al. ............ 526/132 |
| 5,686,625 A | 11/1997 | Kos ............ 548/457 |
| 5,847,059 A * | 12/1998 | Shamshoum et al. ....... 526/116 |
| 6,010,974 A * | 1/2000 | Kim et al. ............ 502/152 |
| 6,143,844 A * | 11/2000 | Hokkanen et al. ......... 526/114 |
| 6,211,311 B1 | 4/2001 | Wang et al. ............ 526/131 |
| 6,521,716 B1 * | 2/2003 | Leake ............ 525/421 |
| 6,693,157 B2 * | 2/2004 | Schuchardt ............ 526/170 |
| 2003/0032549 A1 * | 2/2003 | Vogel |

FOREIGN PATENT DOCUMENTS

DE 1951321 1/1971

OTHER PUBLICATIONS

Reddy et al., *Organometallics* 8 (1989) 2107.
Jungling et al., *J. Organometal, Chem.* 460 (1993) 191.
Soga et al., *J. Mol. Catal. A* 128 (1998) 273.
Noh et al., *J. Organometal, Chem* 580 (1999).
*Colour Index International*, 4th Edition Online—www.colour-index.org.
J. Nakayama et al., *Chem. Lett.* (1977) 77.
H. Junek et al., *Chem. Ber.* 110 (1977) 2276.
M. Augustin et al., *J. Prakt. Chem.* 321 (1979) 205.
Schlosser et at., *Angew. Chem., I.E. Engl.* 12 (1973) 508.
Lochmann et al., *Tetrahedron Lett.* (1966) 257.
R. Gompper et al., *Chem. Ber.* 98 (1965) 1369.
Masatoshi et al. (XP002284956 from STN 2000: 152663) referencing Japanese Patent No. 2000 072810.

* cited by examiner

*Primary Examiner*—Mark L. Bell
*Assistant Examiner*—Jennine M. Brown
(74) *Attorney, Agent, or Firm*—Jonathan L. Schuchardt

(57) ABSTRACT

A catalyst system useful for polymerizing olefins is disclosed. The catalyst system comprises an activator and a bimetallic complex that incorporates two Group 3 to 10 transition metal atoms, which may be the same or different, and a neutral or anionic indigoid ligand. By proper selection of the indigoid skeleton and by modifying its substituents and transition metal centers, polyolefin makers can fine-tune the bimetallic complexes to control activity, enhance comonomer incorporation, and optimize polymer properties.

19 Claims, No Drawings

BIMETALLIC OLEFIN POLYMERIZATION CATALYSTS CONTAINING INDIGOID LIGANDS

FIELD OF THE INVENTION

The invention relates to catalysts useful for olefin polymerization. In particular, the invention relates to bimetallic catalysts that incorporate an indigoid ligand.

BACKGROUND OF THE INVENTION

While Ziegler-Natta catalysts are a mainstay for polyolefin manufacture, single-site (metallocene and non-metallocene) catalysts represent the industry's future. These catalysts are often more reactive than Ziegler-Natta catalysts, and they often produce polymers with improved physical properties.

Since the mid-1980s, scientists have become increasingly interested in bimetallic metallocenes, and in particular, how two metal centers communicate with each other via electronic and through-space interactions (see, e.g., Reddy et al. *Organometallics* 8 (1989) 2107). Cooperative effects are most likely when the two metal centers are electronically coupled through a conjugated pi-electron system. Ultimately, understanding cooperative effects should let polyolefin manufacturers fine-tune polymer properties by varying catalyst structure.

While many interesting bimetallic complexes have been investigated (see, e.g., Jungling et al., *J. Organometal. Chem.* 460 (1993) 191; Soga et al., *J. Mol. Catal. A* 128 (1998) 273; and Noh et al., *J. Organometal. Chem.* 580 (1999), there apparently has been little or no interest in synthesizing bimetallic olefin polymerization catalysts that incorporate indigo and similar compounds ("indigoids") as ligands.

Naturally occurring indigoid dyes have been known for thousands of years. Cloth dyed with indigotin was found in Egyptian tombs and Incan graves. Tyrian Purple, an expensive dye of the ancient world, was painstakingly isolated from mollusks of the Muricidae family. The dyes remained rare and valuable for hundreds of years. In the late nineteenth century, Nobel Prize winner Adolf von Baeyer and other chemists began elucidating dye structures and developing synthetic routes to a wide variety of water-insoluble "vat dyes," including indigoids. By the 1920s, hundreds of indigoid dyes had been synthesized and patented. Some common examples:

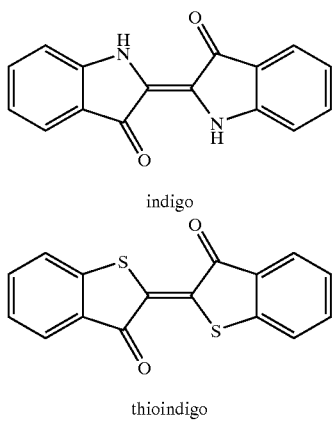

indigo thioindigo

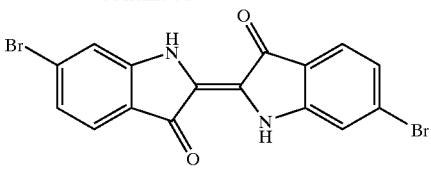

Tyrian Purple

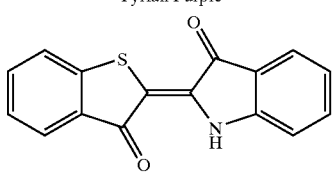

Ciba Violet A

The basic indigo framework has often been elaborated by halogenation, replacement of two nitrogen atoms with sulfur (to make "thioindigoids") replacement of one nitrogen atom with sulfur (to make "indole-naphthenes" such as Ciba Violet A), ring substitution with alkyl, alkoxy, thioalkoxy or other groups, adding benzo-fused rings, and so forth. For a few examples of indigo and indigoid preparation, see U.S. Pat. Nos. 1,133,031, 1,211,413, 1,564,218, 1,590,685, and 1,954,707.

A variety of other interesting compounds, particularly 1,3-diones, are also "indigoids" in the sense that they are isoelectronic with indigo. Like indigo, they contain a cross-conjugated, "H-chromagen" (explained below). Unlike indigo, the carbonyl groups are on the same side of the central carbon-carbon double bond. Like indigo, indigoids based on 1,3-diones have not been incorporated into bimetallic olefin polymerization catalysts.

The polyolefins industry continues to need new polymerization catalysts. Unfortunately, the organometallic complexes are becoming increasingly complicated and more expensive to manufacture. Until now, the synthesis of bimetallic complexes has involved a multistep process to produce a bridged ligand, followed by incorporation of transition metals to give the complex. The industry would benefit from a ready source of ligands suitable for making bimetallic complexes. Ideally, the catalysts would avoid the all-too-common, low-yield, multi-step syntheses from expensive, hard-to-handle starting materials and reagents.

SUMMARY OF THE INVENTION

The invention is a catalyst system useful for polymerizing olefins. The catalyst system comprises an activator and a bimetallic complex. The complex comprises two Group 3–10 transition metal atoms, which may be the same or different, and a neutral or anionic indigoid ligand.

Because indigoid dyes have been synthetic targets for over 100 years, a wide variety of indigoids are commercially available or are easily prepared. By judiciously selecting the indigoid skeleton and by modifying its substituents and transition metal centers, polyolefin makers can fine-tune the bimetallic complexes to control activity, enhance comonomer incorporation, and optimize polymer properties.

DETAILED DESCRIPTION OF THE INVENTION

Catalyst systems of the invention include a bimetallic complex that contains two Group 3–10 transition metal atoms, which may be the same or different. "Transition metal" as used herein includes, in addition to the main transition group elements, elements of the lanthanide and actinide series. More preferred complexes include a Group 4 or a Group 8 to 10 transition metal.

The bimetallic complex includes a neutral or anionic indigoid ligand. By "indigoid," we mean ligands derived from indigo and compounds that are isoelectronic with indigo. Compounds that are "isoelectronic" with indigo possess, like indigo, a cross-conjugated moiety in which five electron pairs are oriented roughly in the shape of a capital "H." In indigo, this is known as an "H-chromagen":

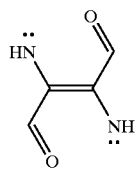

an "H-chromagen"

The indigoid framework can be substituted with other atoms that do not interfere with the ability of the indigoid or its deprotonated counterpart to form bimetallic complexes with transition metals. For example, the indigoid can be substituted with alkyl, aryl, halide, alkoxy, thioether, alkylsilyl, or other groups.

Indigoid ligands are made by any suitable method. As noted earlier, a large number of indigoid compounds have been manufactured for use as dyes, and many synthetic approaches have been developed. For examples of indigo and indigoid preparation, see U.S. Pat. Nos. 622,139, 718, 340, 765,576, 1,211,413, 1,564,218, 4,966,977, 5,686,625 (indigo); U.S. Pat. Nos. 662,073, 872,115, 872,227, 856, 687, 899,863 (substituted indigos); U.S. Pat. Nos. 949,592, 1,133,031 (thioindigo); U.S. Pat. Nos. 848,354, 867,306, 867,715, 888,852, 916,030, 963,813, 1,954,707 (substituted thioindigos); U.S. Pat. Nos. 836,309, 841,003, 892,897, and 1,590,685 (indole-thianaphthenes), the teachings of which are incorporated herein by reference.

Indigoid dyes have been catalogued and classified by the Society of Dyers and Colourists and the American Association of Textile Chemists and Colorists (AATCC). See, especially, the *Colour Index International, 4th Edition Online*, which is now available to subscribers at www.colour-index.org. Indigoids have Colour Index (CI) numbers 73000 to 73999. This reference is a valuable source of a wide variety of indigoid syntheses.

Preferred indigoids include indigos, indole-naphthenes (like indigos, but replacing one N with S), thioindigos (replace both Ns with S), 1,3-diones or 1,3-dithiones that possess an H-chromagen, and bisimines derived from any of the above.

As noted above, the indigoid ligands may be neutral or anionic. When the complex incorporates an early transition metal (i.e., Groups 3–5), the indigoid ligand will normally be anionic. Neutral indigoid ligands are generally used only with late transition metals (i.e., Groups 8–10). However, late transition metals can be, and often are, present in complexes based on anionic indigoids. Note that the bimetallic complexes may contain early transition metals, late transition metals, or one of each.

Among neutral indigoid ligands, preferred ones have the structure:

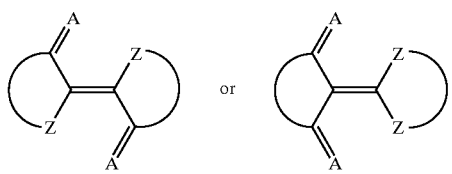

in which each A is independently O, NR, or S; each Z is independently O, NR, or S; R is hydrogen or a $C_1$–$C_{20}$ alkyl or aryl group; and each of the two rings includes 4 to 7 atoms.

The neutral indigoid ligand may be a bisimine. Preferred indigoid bisimine ligands have the structures noted above in which each A is independently NR. Particularly preferred bisimine indigoid ligands derive from indigo and have the structure:

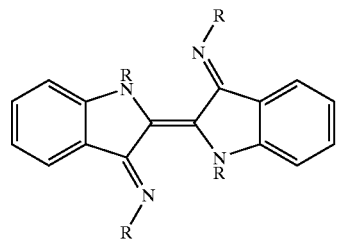

in which each R is independently hydrogen or a $C_1$–$C_{20}$ alkyl or aryl group.

Suitable neutral "indigoid" ligands also include 1,3-diones (and bisimines derived from the 1,3-diones) that are isoelectronic with indigo. Like indigo, these compounds incorporate an "H-chromagen." Some examples:

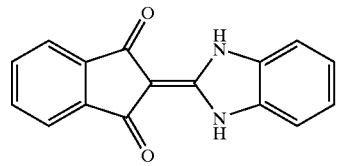

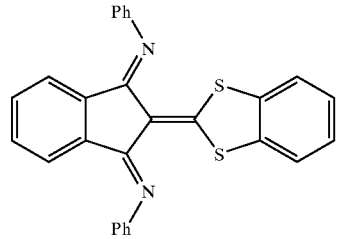

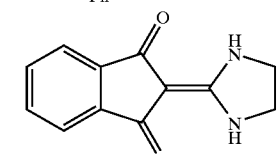

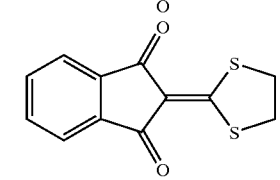

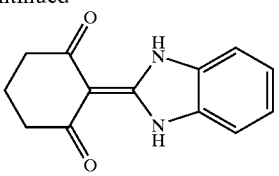

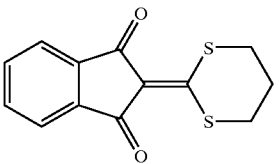

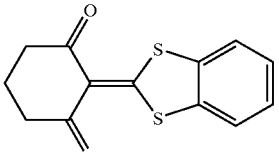

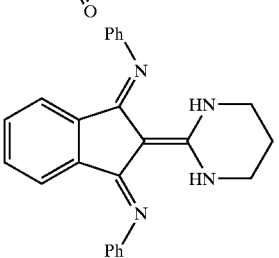

For more examples of these "indigoids" and synthetic routes to them, see J. Nakayama et al., *Chem. Lett.* (1977) 77; H. Junek et al., *Chem. Ber.* 110 (1977) 2276; and M. Augustin et al., *J. Prakt. Chem.* 321 (1979) 205.

A preferred class of neutral indigoid ligands based on 1,3-diones has the structure:

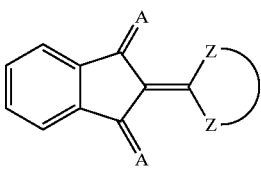

in which each A is independently O, or NR; each Z is independently O, NR, or S; R is hydrogen or a $C_1$–$C_{20}$ alkyl or aryl group; and the ring containing the Z atoms includes 4 to 7 atoms.

In another preferred class, the neutral indigoid ligand has the structure:

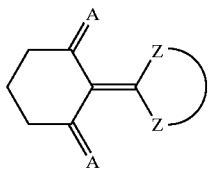

in which A and Z have the meanings given above, and the ring containing the Z atoms includes 4 to 7 atoms.

As noted earlier, the indigoid ligand can be—and preferably is—anionic. Anionic indigoid ligands can be used with any of the Group 3–10 transition metals. Preferred anionic indigoid ligands have the structure:

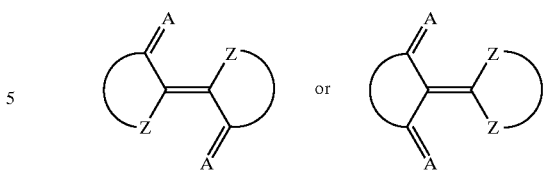

in which each A is independently O, NR, N—, or S; each Z is independently O, NR, N—, or S; R is hydrogen or a $C_1$–$C_{20}$ alkyl or aryl group; and each of the two rings includes 4 to 7 atoms. Consistent with the requirement of being "anionic," at least one of A or Z is N—.

In particularly preferred catalyst systems of the invention, the indigoid ligand is dianionic. Preferred dianionic indigoid ligands have the structures noted above wherein Z is N— and each A is independently O, S, or NR.

Dianionic indigoid ligands are normally generated by deprotonating an amine precursor with about two equivalents of a potent base (alkyllithium, Grignard reagent, alkali metal hydride, or the like). A preferred dianionic indigoid ligand derives from indigo and has the structure:

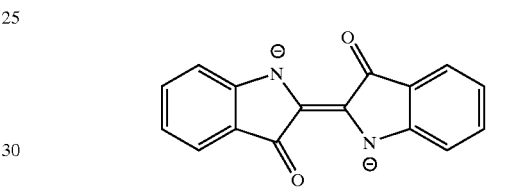

In other preferred catalyst systems, the dianionic indigoid ligand is a bisimine. The bisimine compounds are easily prepared by condensing the corresponding dicarbonyl compound with two equivalents of a primary amine, preferably a primary aromatic amine. Preferred bisimines have the structures noted earlier for anionic indigoid ligands wherein each A is independently NR, and each Z is N—. Particularly preferred dianionic bisimines are based on indigo and have the structure:

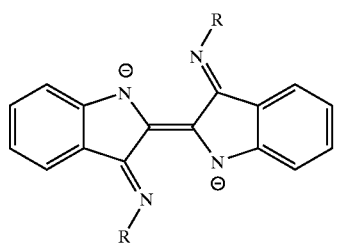

in which each R is independently a $C_1$–$C_{30}$ alkyl or aryl group.

Suitable dianionic indigoids include those derived from the 1,3-diones (and their bisimine derivatives) described earlier. A few examples:

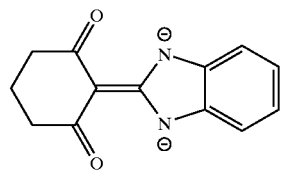

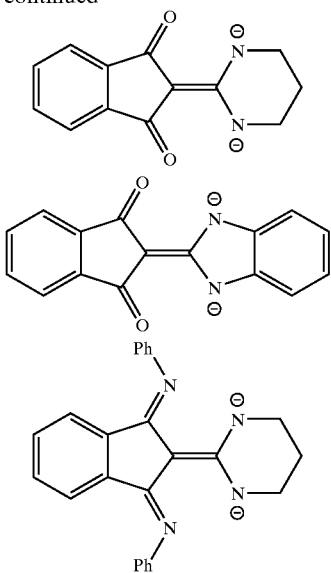

A preferred class of dianionic indigoid ligands based on 1,3-diones has the structure:

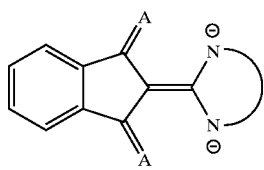

in which each A is independently O or NR; R is hydrogen or a $C_1$–$C_{20}$ alkyl or aryl group; and the ring containing the N atoms includes 4 to 7 atoms.

In another preferred class, the dianionic ligands have the structure:

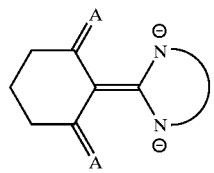

in which each A is independently O or NR; R is hydrogen or a $C_1$–$C_{20}$ alkyl or aryl group; and the ring containing the N atoms includes 4 to 7 atoms.

Dianionic indigoid ligands are conveniently made by doubly deprotonating the corresponding amine precursor with a potent base according to well-known methods. Suitable bases include, for example, alkyllithium compounds (e.g., methyllithium or n-butyllithium), alkali metals (e.g., sodium metal), alkali metal hydrides (e.g., potassium hydride), and Grignard reagents (e.g., methyl magnesium chloride or phenyl magnesium bromide). Particularly preferred deprotonating agents are super-basic reagents prepared by the reaction of alkyllithium compounds and alkali metal t-butoxides, as reported by Schlosser et al. (*Angew. Chem., I.E. Engl.* 12 (1973) 508) and Lochmann et al. (*Tetrahedron Lett.* (1966) 257).

Usually, about two equivalents of the deprotonating agent and about one equivalent of the precursor are used to produce the dianionic ligand. Deprotonation can be performed at any suitable temperature, preferably at or below room temperature. While the deprotonation reaction can be performed at temperatures as low as −78° C. or below, it is preferred to perform this step at room temperature.

In addition to the indigoid ligand, the bimetallic complex may include additional labile anionic ligands such as halides, alkyls, alkaryls, aryls, dialkylaminos, or the like. Particularly preferred are halides, alkyls, and alkaryls (e.g., chloride, methyl, benzyl).

The bimetallic complexes are prepared according to methods that are well known in the art. In general, the complexes are made by combining the neutral or anionic indigoid ligand with a transition metal source. Any convenient source of transition metal can be used. For example, the complexes can be made from transition metal halides, alkyls, alkoxides, acetates, amides, or the like. A particularly convenient source of the transition metal is the transition metal halide. For example, one can use titanium tetrachloride, zirconium tetrachloride, cyclopentadienylzirconium trichloride, vanadium(III) chloride-tetrahydrofuran complex ($VCl_3$(THF)$_3$), titanium (III) chloride-THF complex, chromium (III) chloride-THF complex, cobalt(II) chloride, nickel(II) bromide, platinum(II) chloride, allylnickel(II) chloride dimer, palladium(II) chloride, lanthanum(III) chloride, titanium(III) acetate, or the like. Complexes can also be prepared from salts with labile groups, such as tetrakis(acetonitrile)palladium(II) bis(tetrafluoroborate).

The transition metal complexes are easy to make. Usually, the transition metal source (halide, e.g.) is dissolved or suspended in an organic solvent and the neutral or anionic indigoid ligand is carefully added at any desired temperature, preferably from about −78° C. to about room temperature. Refluxing is used if needed to complete the reaction. Insoluble by-products, if any, can be removed by filtration, solvents are evaporated, and the transition metal complex is isolated, washed, and dried. The resulting complex can generally be used without further purification. Examples 1–7 below illustrate a few suitable methods for making the bimetallic complexes.

Exemplary bimetallic complexes useful in the catalyst systems:

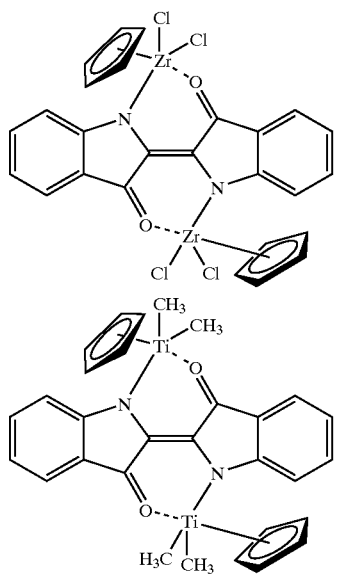

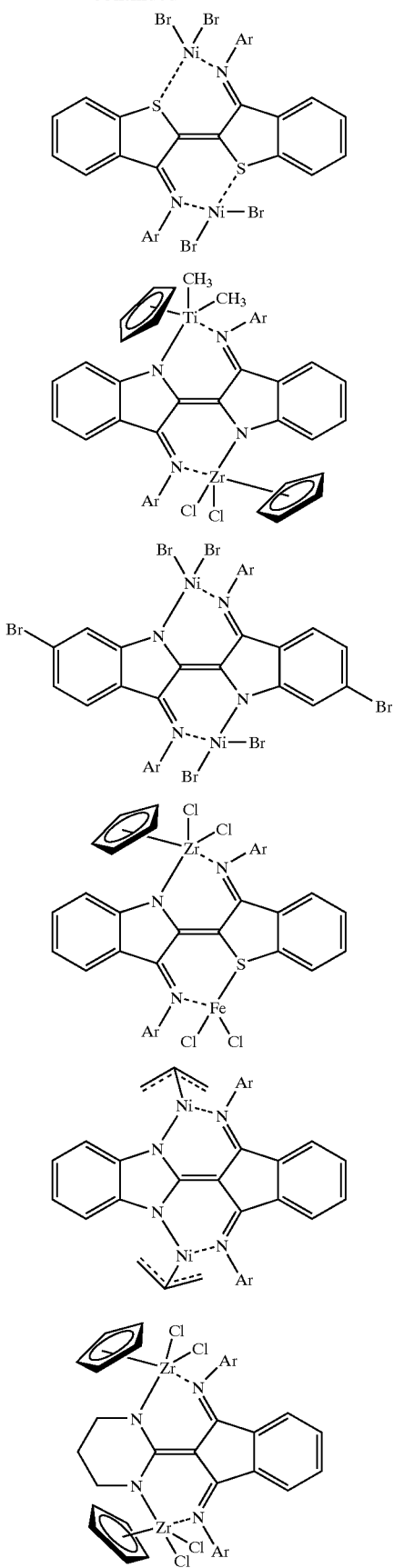
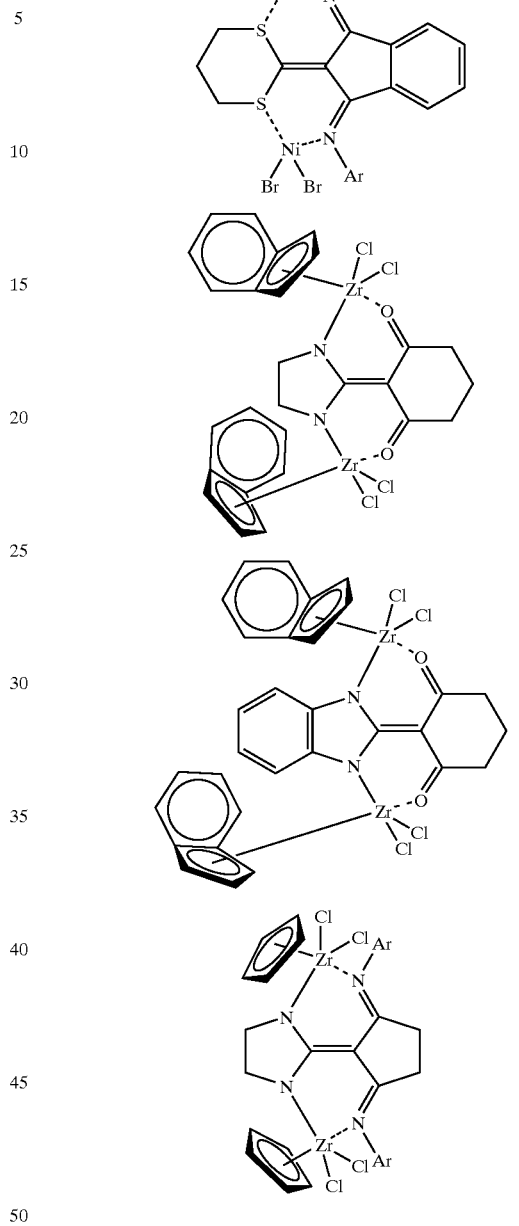

In sum, the a wide variety of indigoid complexes are readily accessible for use in catalyst systems of the invention. The complexes and methods discussed above for making them are merely illustrative, and those skilled in the art will readily recognize or devise many alternative synthetic methodologies.

The catalyst systems include an activator. Suitable activators help to ionize the bimetallic complex and activate the catalyst. Suitable activators are well known in the art. Examples include alumoxanes (methyl alumoxane (MAO), PMAO, ethyl alumoxane, diisobutyl alumoxane), alkylaluminum compounds (triethylaluminum, diethyl aluminum chloride, trimethylaluminum, triisobutyl aluminum), and the like. Suitable activators include acid salts that contain non-nucleophilic anions. These compounds generally consist of bulky ligands attached to boron or aluminum. Examples include lithium tetrakis(pentafluorophenyl)borate, lithium tetrakis(pentafluorophenyl)aluminate, anilinium tetrakis (pentafluorophenyl)borate, and the like. Suitable activators also include organoboranes, which include boron and one or more alkyl, aryl, or aralkyl groups. Suitable activators include substituted and unsubstituted trialkyl and triarylboranes such as tris(pentafluorophenyl)borane, triphenylborane, tri-n-octylborane, and the like. These and other suitable boron-containing activators are described in U.S. Pat. Nos. 5,153,157, 5,198,401, and 5,241,025, the teachings of which are incorporated herein by reference. Suitable activators also include aluminoboronates—reaction products of alkyl aluminum compounds and organoboronic acids—as described in U.S. Pat. Nos. 5,414,180 and 5,648,440, the teachings of which are incorporated herein by reference.

The optimum amount of activator needed relative to the amount of bimetallic complex depends on many factors, including the nature of the complex and activator, whether a supported catalyst is used, the desired reaction rate, the kind of polyolefin product, the reaction conditions, and other factors. Generally, however, when the activator is an alumoxane or an alkyl aluminum compound, the amount used will be within the range of about 0.01 to about 5000 moles, preferably from about 10 to about 500 moles, of aluminum per mole of transition metal, M. When the activator is an organoborane or an ionic borate or aluminate, the amount used will be within the range of about 0.01 to about 5000 moles, preferably from about 0.1 to about 500 moles, of activator per mole of M.

The activator is normally added to the reaction mixture at the start of the polymerization. However, when a supported catalyst system is used, the activator can be deposited onto the support along with the bimetallic complex.

The catalyst systems are optionally used with an inorganic solid or organic polymer support. Suitable supports include silica, alumina, silica-aluminas, magnesia, titania, clays, zeolites, or the like. The support is preferably treated thermally, chemically, or both prior to use to reduce the concentration of surface hydroxyl groups. Thermal treatment consists of heating (or "calcining") the support in a dry atmosphere at elevated temperature, preferably greater than about 100° C., and more preferably from about 150 to about 600° C., prior to use. A variety of different chemical treatments can be used, including reaction with organo-aluminum, -magnesium, -silicon, or -boron compounds. See, for example, the techniques described in U.S. Pat. No. 6,211,311, the teachings of which are incorporated herein by reference.

The complex and activator can be deposited on the support in any desired manner. For instance, the components can be dissolved in a solvent, combined with a support, and stripped. Alternatively, an incipient-wetness technique can be used. Moreover, the support can simply be introduced into the reactor separately from the complex and activator.

The loading of complex on the support varies depending upon a number of factors, including the identities of the complex and the support, the type of olefin polymerization process used, the reaction conditions, and other concerns. Usually, the amount of complex used is within the range of about 0.01 to about 10 wt. % of transition metal based on the amount of supported catalyst. A more preferred range is from about 0.1 to about 4 wt. %.

Catalyst systems of the invention are useful for polymerizing olefins. Preferred olefins are ethylene and $C_3$–$C_{20}$ α-olefins such as propylene, 1-butene, 1-hexene, 1-octene, and the like. Mixtures of olefins can be used. Ethylene and mixtures of ethylene with $C_3$–$C_{10}$ α-olefins are, especially preferred.

Many types of olefin polymerization processes can be used. Preferably, the process is practiced in the liquid phase, which can include slurry, solution, suspension, or bulk processes, or a combination of these. High-pressure fluid phase or gas phase techniques can also be used. The process of the invention is particularly valuable for solution and slurry processes.

The olefin polymerizations can be performed over a wide temperature range, such as about −30° C. to about 280° C. A more preferred range is from about 30° C. to about 180° C.; most preferred is the range from about 60° C. to about 100° C. Olefin partial pressures normally range from about 15 psig to about 50,000 psig. More preferred is the range from about 15 psig to about 1000 psig.

The following examples merely illustrate the invention. Those skilled in the art will recognize many variations that are within the spirit of the invention and scope of the claims.

EXAMPLE 1

Preparation of Bimetallic Complex 1

Indigo (262 mg, 1.0 mmol) in dry diethyl ether (25 mL) is doubly deprotonated by careful addition of n-butyllithium (1.3 mL of 1.6 M solution in hexanes, 2.1 mmol) at −78° C. The mixture warms to about 0° C., and the resulting dianion is separated from excess salts by filtration in vacuo.

The indigoid dianion solution is added by cannula to a stirred slurry of cyclopentadienyl zirconium trichloride (526 mg, 2.0 mmol) in diethyl ether (25 mL) at −78° C. The reaction mixture is stirred and allowed to warm to room temperature. Volatiles are removed in vacuo. The residue is extracted with toluene to give a solution of the organometallic complex. The expected product is complex 1:

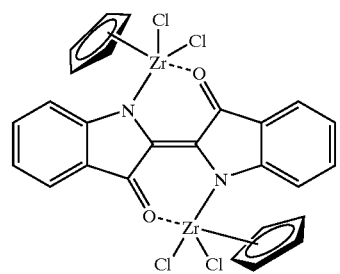

EXAMPLE 2

Preparation of Bimetallic Complex 2

Thioindigo (296 mg, 1.0 mmol) is dissolved in dry toluene (20 mL). Aniline (191 mg, 2.05 mmol) is added, followed by a drop of formic acid, and the mixture is stirred at room temperature overnight. The mixture is diluted with diethyl ether (50 mL) and washed with water (10 mL) and saturated aqueous sodium chloride (10 mL). The organic phase is then dried over anhydrous magnesium sulfate, filtered, and concentrated.

The residue is dissolved in dry tetrahydrofuran (30 mL), and iron(II) chloride (250 mg, 2.0 mmol) is added. The mixture is stirred for 24 h under nitrogen at room temperature. The liquid phase is removed by filtration, and the solids are dried under vacuum for 1 h. The resulting complex (2) is expected to have the structure:

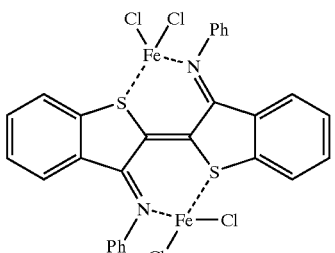

2

EXAMPLE 3

Preparation of Bimetallic Complex 3

Indigo (262 mg, 1.0 mmol) is dissolved in dry toluene (20 mL). Aniline (191 mg, 2.05 mmol) is added, followed by a drop of formic acid, and the mixture is stirred at room temperature overnight. The mixture is diluted with diethyl ether (50 mL) and washed with water (10 mL) and saturated aqueous sodium chloride (10 mL). The organic phase is then dried over anhydrous magnesium sulfate, filtered, and concentrated to give a bis(imine) derivative of indigo.

The bis(imine) is dissolved in dry diethyl ether (25 mL) and is then doubly deprotonated by careful addition of n-butyllithium (1.3 mL of 1.6 M solution in hexanes, 2.1 mmol) at −78° C. The mixture warms to about 0° C., and the resulting dianion is separated from excess salts by filtration in vacuo.

A mixture of allylnickel(II) chloride dimer (270 mg, 1.0 mmol) in diethyl ether (25 mL) is prepared and cooled to 0° C. The bis(imine) dianion solution is carefully transferred by cannula to the transition metal mixture, and the product is stirred for 2 h under nitrogen while warming to room temperature. Solvents are removed by vacuum stripping. The resulting complex (3) is expected to have the structure:

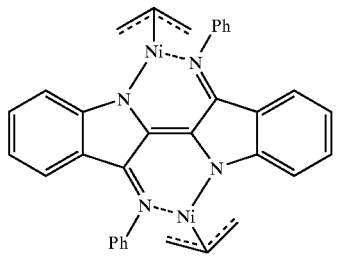

3

EXAMPLE 4

Preparation of Bimetallic Complex 6

2-(1,3-Dioxo-2-indanylidene)imidazoline (5) is prepared according to the method of H. Junek et al. (*Chem. Ber.* 110 (1977) 2276). Thus, a flask is charged with 2-dicyanomethylene-1,3-indandione (4) (400 mg, 2.0 mmol) and methanol (80 mL). Ethylenediamine (120 µL, 2.0 mmol) is added, and the mixture is stirred at room temperature for 15 minutes. The methanol is removed by vacuum stripping, and the crude product is recrystallized from xylenes.

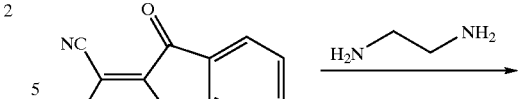

4

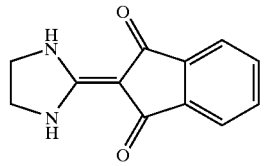

5

A portion of the recrystallized imidazoline compound 5 (214 mg, 1.0 mmol) in dry diethyl ether (25 mL) is doubly deprotonated by careful addition of n-butyllithium (1.3 mL of 1.6 M solution in hexanes, 2.1 mmol) at −78° C. The mixture warms to about 0° C., and the resulting dianion is separated from excess salts by filtration in vacuo.

The dianion solution is added by cannula to a stirred slurry of cyclopentadienyl zirconium trichloride (526 mg, 2.0 mmol) in diethyl ether (25 mL) at −78° C. The reaction mixture is stirred and allowed to warm to room temperature. Volatiles are removed in vacuo. The residue is extracted with toluene to give a solution of the organometallic complex. The resulting complex (6) is expected to have the structure:

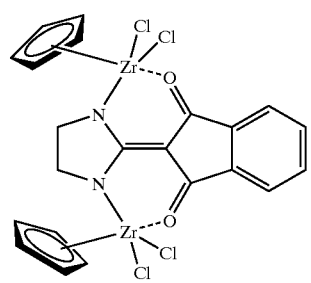

6

EXAMPLE 5

Preparation of Bimetallic Complex 9

The method of M. Augustin et al. (*J. Prakt. Chem.* 321 (1979) 205) is used to prepare 2-(1,3-dioxo-2-indanylidene) benzimidazoline (8). First, indan-1,3-dione reacts with an equimolar amount of carbon disulfide in the presence of two equivalents of sodium t-pentoxide in dimethylformamide, followed by careful reaction with bromomethane to give 2-[bis(methylthio)methylidene]-indan-1,3-dione (7). Reaction of 7 with 1,2-phenylenediamine in refluxing ethanol, also following Augustin's procedure gives the benzimidazoline 8.

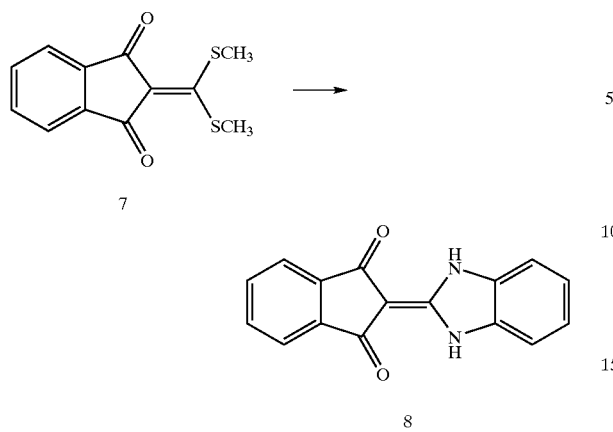

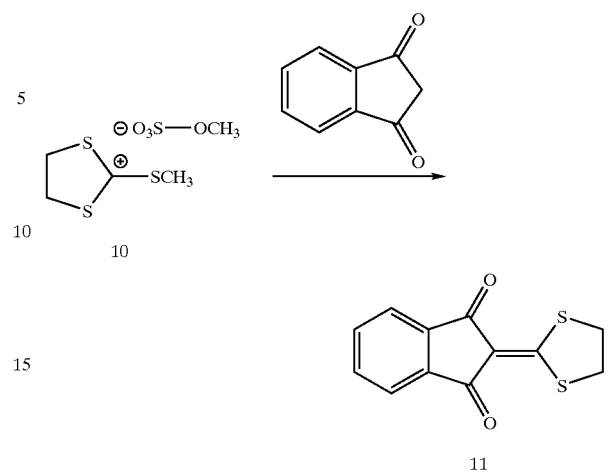

A sample of benzimidazoline compound 8 (262 mg, 1.0 mmol) is dissolved in dry toluene (20 mL). Aniline (191 mg, 2.05 mmol) is added, followed by a drop of formic acid, and the mixture is stirred at room temperature overnight. The mixture is diluted with diethyl ether (50 mL) and washed with water (10 mL) and saturated aqueous sodium chloride (10 mL). The organic phase is then dried over anhydrous magnesium sulfate, filtered, and concentrated to give a bis(imine) compound.

The bis(imine) is dissolved in dry diethyl ether (25 mL) and is then doubly deprotonated by careful addition of n-butyllithium (1.3 mL of 1.6 M solution in hexanes, 2.1 mmol) at −78° C. The mixture warms to about 0° C., and the resulting dianion is separated from excess salts by filtration in vacuo.

The dianion solution is added by cannula to a stirred slurry of cyclopentadienyl zirconium trichloride (526 mg, 2.0 mmol) in diethyl ether (25 mL) at −78° C. The reaction mixture is stirred and allowed to warm to room temperature. Volatiles are removed in vacuo. The residue is extracted with toluene to give a solution of the organometallic complex. The resulting complex (9) is expected to have the structure:

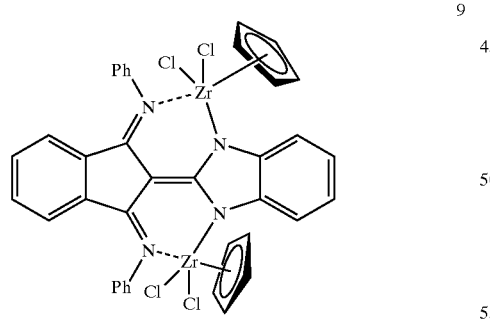

EXAMPLE 6

Preparation of Bimetallic Complex 12

The method of J. Nakayama et al. (*Chem. Letters* (1977) 77) is used to prepare 2-(1,3-dithiolan-2-ylidene)-1,3-indandione (11). Thus, 2-methylthio-1,3-dithiolanylium methylsulfate (10) prepared according to the procedure of R. Gompper et al. (*Chem. Ber.* 98 (1965) 1369) is reacted with an equivalent of 1,3-indandione to give 11.

A sample of the indandione 11 (248 mg, 1.0 mmol) is dissolved in dry toluene (20 mL). Aniline (191 mg, 2.05 mmol) is added, and the mixture is heated to reflux for 3 h with water removal. The mixture is cooled, then diluted with diethyl ether (50 mL) and washed with water (10 mL) and saturated aqueous sodium chloride (10 mL). The organic phase is then dried over anhydrous magnesium sulfate, filtered, and concentrated.

The residue is dissolved in dry tetrahydrofuran (30 mL), and anhydrous nickel(II) bromide (437 mg, 2.0 mmol) is added. The mixture is stirred for 24 h under nitrogen at room temperature. The liquid phase is removed by filtration, and the solids are dried under vacuum for 1 h. The resulting complex (12) is expected to have the structure:

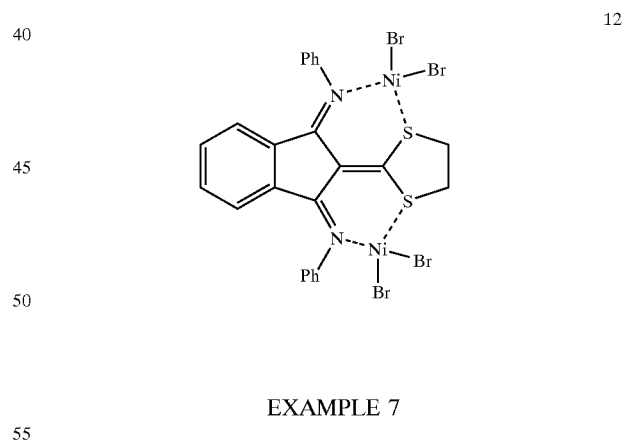

EXAMPLE 7

Preparation of Bimetallic Complex 15

The method of M. Augustin et al. (*J. Prakt. Chem.* 321 (1979) 205) is used to prepare imidazolinylidenyl-cyclopentan-1,3-dione (14). First, cyclopentan-1,3-dione reacts with an equimolar amount of carbon disulfide in the presence of two equivalents of sodium t-pentoxide in dimethylformamide, followed by careful reaction with bromomethane to give ylidenedithioether 13. Reaction of 13 with ethylenediamine in refluxing ethanol gives 14.

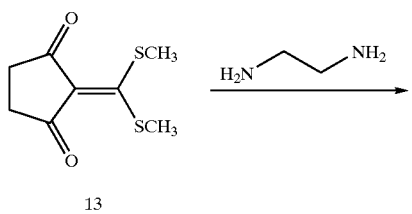

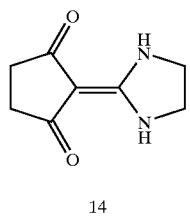

A sample of 14 (166 mg, 1.0 mmol) is dissolved in dry toluene (20 mL). Aniline (191 mg, 2.05 mmol) is added, and the mixture is heated to reflux for 3 h with water removal. The mixture is cooled, then diluted with diethyl ether (50 mL) and washed with water (10 mL) and saturated aqueous sodium chloride (10 mL). The organic phase is then dried over anhydrous magnesium sulfate, filtered, and concentrated to give a bis(imine) compound.

The bis(imine) is dissolved in dry diethyl ether (25 mL) and is then doubly deprotonated by careful addition of n-butyllithium (1.3 mL of 1.6 M solution in hexanes, 2.1 mmol) at −78° C. The mixture warms to about 0° C., and the resulting dianion is separated from excess salts by filtration in vacuo.

The dianion solution is added by cannula to a stirred slurry of cyclopentadienyl zirconium trichloride (526 mg, 2.0 mmol) in diethyl ether (25 mL) at −78° C. The reaction mixture is stirred and allowed to warm to room temperature. Volatiles are removed in vacuo. The residue is extracted with toluene to give a solution of the organometallic complex. The resulting complex (15) is expected to have the structure:

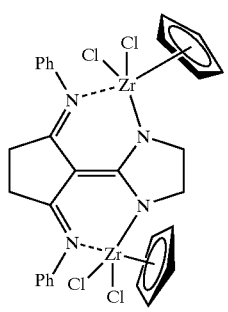

EXAMPLE A

Polyethylene Preparation—General Procedure

Methyl alumoxane (5 mL of 10 wt. % MAO in toluene) is added to a 200-mg sample of any of the indigoid complexes prepared in Examples 1–7. The mixture is injected into a 1.7-L stainless-steel autoclave containing dry, deoxygenated isobutane (850 mL) and triisobutylaluminum (0.2 mmol). The autoclave is heated to 80° C. and is pressurized with ethylene (150 psi). After 1 h, the autoclave is cooled, isobutane is flashed off. In each case, the resulting product should be polyethylene.

The preceding examples are meant only as illustrations. The following claims define the invention.

We claim:

1. A catalyst system which comprises:
   (a) an activator; and
   (b) a bimetallic complex comprising two Group 3–10 transition metal atoms, which may be the same or different, and a neutral or anionic indigoid ligand.

2. The catalyst system of claim 1 wherein the activator is selected from the group consisting of alkyl alumoxanes, alkylaluminum compounds, aluminoboronates, organoboranes, ionic borates, and ionic aluminates.

3. The catalyst system of claim 1 comprising a Group 4 metal.

4. The catalyst system of claim 1 comprising a Group 8–10 metal.

5. The catalyst system of claim 4 wherein the indigoid ligand is neutral and has the structure:

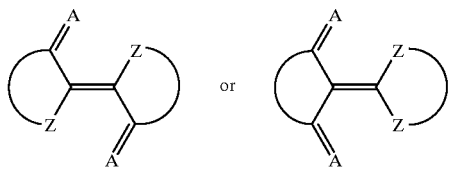

in which each A is independently O, NR, or S; each Z is independently O, NR, or S; R is hydrogen or a $C_1$–$C_{20}$ alkyl or aryl group; and each of the two rings includes 4 to 7 atoms.

6. The catalyst system of claim 5 wherein the neutral indigoid ligand is a bisimine in which each A is independently NR.

7. The catalyst system of claim 6 wherein the neutral indigoid ligand has the structure:

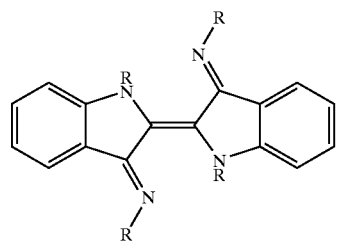

in which each R is independently hydrogen or a $C_1$–$C_{20}$ alkyl or aryl group.

8. The catalyst system of claim 5 wherein the neutral indigoid ligand has the structure:

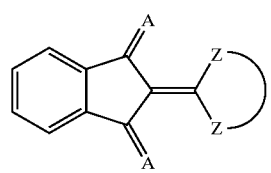

in which each A is independently O or NR.

9. The catalyst system of claim 5 wherein the neutral indigoid ligand has the structure:

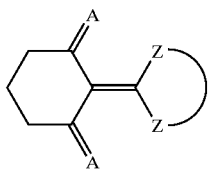

in which each A is independently O or NR.

10. The catalyst system of claim 1 wherein the indigoid ligand is anionic and has the structure:

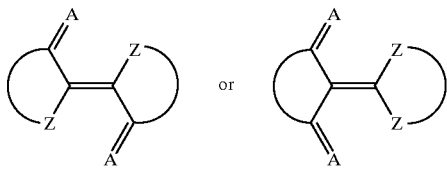

in which each A is independently O, NR, N—, or S; each Z is independently O, NR, N—, or S; R is hydrogen or a $C_1$–$C_{20}$ alkyl or aryl group; and each of the two rings includes 4 to 7 atoms.

11. The catalyst system of claim 10 wherein the indigoid ligand is dianionic.

12. The catalyst system of claim 11 wherein the dianionic indigoid ligand has the structure:

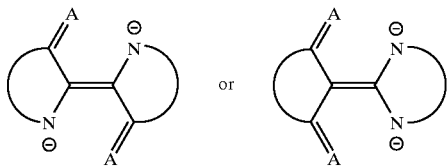

in which each A is independently O, NR, or S.

13. The catalyst system of claim 12 wherein the dianionic indigoid ligand has the structure:

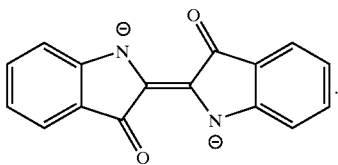

14. The catalyst system of claim 12 wherein the dianionic indigoid ligand is a bisimine in which each A is independently NR.

15. The catalyst system of claim 14 wherein the dianionic indigoid ligand has the structure:

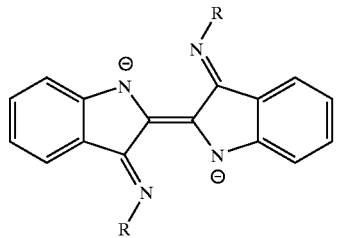

in which each R is independently hydrogen or a $C_1$–$C_{20}$ alkyl or aryl group.

16. The catalyst system of claim 11 wherein the dianionic indigoid ligand has the structure:

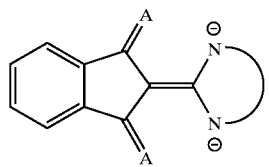

in which each A is independently O or NR.

17. The catalyst system of claim 11 wherein the dianionic indigoid ligand has the structure:

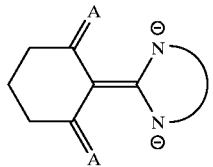

in which each A is independently O or NR.

18. A process which comprises polymerizing an olefin in the presence of the catalyst system of claim 1.

19. A process which comprises polymerizing ethylene with at least one alpha-olefin in the presence of the catalyst system of claim 1.

* * * * *